(12) United States Patent
Cohen Maimon et al.

(10) Patent No.: US 10,818,013 B2
(45) Date of Patent: Oct. 27, 2020

(54) SYSTEMS AND METHODS FOR PROCESSING DATA EXTRACTED FROM FRAMES CAPTURED FROM VIDEO SIGNALS

(71) Applicant: NEC Corporation Of America, Herzlia (IL)

(72) Inventors: Maya Cohen Maimon, Safed (IL); Tsvi Lev, Tel-Aviv (IL)

(73) Assignee: NEC Corporation Of America, Herzlia (IL)

( * ) Notice: Subject to any disclaimer, the term of this patent is extended or adjusted under 35 U.S.C. 154(b) by 0 days.

(21) Appl. No.: 16/266,069

(22) Filed: Feb. 3, 2019

(65) Prior Publication Data

US 2020/0250826 A1 Aug. 6, 2020

(51) Int. Cl.
*G06T 7/00* (2017.01)
*G16H 30/40* (2018.01)
*G16H 30/20* (2018.01)
*G06T 15/08* (2011.01)
(Continued)

(52) U.S. Cl.
CPC .......... *G06T 7/0016* (2013.01); *G06F 3/0481* (2013.01); *G06K 9/00711* (2013.01); *G06T 15/08* (2013.01); *G16H 30/20* (2018.01); *G16H 30/40* (2018.01); *G06K 2209/01* (2013.01); *G06K 2209/27* (2013.01); *G06T 2207/10016* (2013.01)

(58) Field of Classification Search
None
See application file for complete search history.

(56) References Cited

U.S. PATENT DOCUMENTS 10,163,028 B2 * 12/2018 Rubens ................ G06K 9/4604
2008/0025583 A1 * 1/2008 Jabri ......................... G06T 5/00
382/128
(Continued)

OTHER PUBLICATIONS

Crane, Jason C., Marram P. Olson, and Sarah J. Nelson. "SIVIC: open-source, standards-based software for DICOM MR spectroscopy workflows." International journal of biomedical imaging 2013 (2013).*

(Continued)

*Primary Examiner* — Ryan M Gray

(57) ABSTRACT

There is provided a medical imaging processing device, comprising: at least one hardware processor executing a code for: iteratively generating instructions for iterative adjustment of presentation parameter(s) of a 2D frame of the 3D anatomical image presented on the display, for creating a sequence of adapted 2D frames of the 3D anatomical image, the instructions transmitted from the medical imaging processing device to a physical input interface of at least one of the client terminal and display, for each respective 2D frame: capturing the respective 2D frame from video signals transmitted from the client terminal to the display, analyzing the respective captured 2D frame for extraction of a 2D anatomical image, analyzing the respective captured 2D frame to identify metadata element(s), converting the metadata element(s) into converted metadata value(s), and formatting the extracted 2D anatomical images and associated converted metadata values for reconstruction of the 3D anatomical image.

18 Claims, 4 Drawing Sheets

(51) Int. Cl.
*G06F 3/0481* (2013.01)
*G06K 9/00* (2006.01)

(56) References Cited

U.S. PATENT DOCUMENTS

| | | | |
|---|---|---|---|
| 2013/0129198 A1* | 5/2013 | Sherman | G06F 19/321 |
| | | | 382/159 |
| 2016/0062956 A1* | 3/2016 | Gotman | G06F 40/186 |
| | | | 715/243 |
| 2018/0068466 A1* | 3/2018 | Bronkalla | A61B 6/585 |
| 2019/0051420 A1* | 2/2019 | Zhao | G16H 50/20 |
| 2019/0164285 A1* | 5/2019 | Nye | G06T 7/0014 |
| 2019/0180861 A1* | 6/2019 | Reicher | G16H 40/63 |
| 2019/0269384 A1* | 9/2019 | Lundberg | A61B 8/5223 |
| 2020/0043616 A1* | 2/2020 | Saalbach | G16H 20/40 |

OTHER PUBLICATIONS

Epiphan Systems "Frame Grabber: Capture Up to 60 Frames per Second of Video", Epiphan Systems, Video, 2019.
Traish et al. "Data Collection With Screen Capture", University of Kent, UK, 4 P., Jan. 2015.

* cited by examiner

SYSTEMS AND METHODS FOR PROCESSING DATA EXTRACTED FROM FRAMES CAPTURED FROM VIDEO SIGNALS

FIELD AND BACKGROUND OF THE INVENTION

The present invention, in some embodiments thereof, relates to image processing, more specifically, but not exclusively, to systems and methods for processing data extracted from frames captured from video signals of a display.

Data presented on a display may be obtained in different ways. For example, by performing a screen capture operations, using build in APIs (application programming interfaces) that capture contents of a window presented on the screen, and/or by client code that integrates with the application that presents the data on the screen, to access the original data. The obtained data may be used in different ways, for example, forwarded for presentation on another display, and/or processed by another application designed for compatibility with the client code that obtains the original data and/or designed for compatibility with the format that the original data is stored in.

SUMMARY OF THE INVENTION

According to a first aspect, a medical imaging processing device for reconstruction of a 3D anatomical image from captured 2D frames presented on a display of a client terminal, the medical imaging processing device being external to the display and the client terminal, comprises: at least one hardware processor executing a code for: iteratively generating instructions for iterative adjustment of at least one presentation parameter of a 2D frame of the 3D anatomical image presented on the display, for creating a sequence of adapted 2D frames of the 3D anatomical image, the instructions transmitted from the medical imaging processing device to a physical input interface of at least one of the client terminal and display, for each respective 2D frame: capturing the respective 2D frame from video signals transmitted from the client terminal to the display, analyzing the respective captured 2D frame for extraction of a 2D anatomical image, analyzing the respective captured 2D frame to identify at least one metadata element, converting the at least one metadata element into at least one converted metadata value, and formatting a plurality of the extracted 2D anatomical images and associated plurality of converted metadata values for reconstruction of the 3D anatomical image.

According to a second aspect, a medical data processing device for generation of instructions based on data presented within a plurality of medical UIs presented on a plurality of display of a plurality of client terminal, comprises: at least one hardware processor executing a code for: capturing a certain frame of a video stream of a certain medical UI presented on a certain display of a certain client terminal, analyzing the certain frame to identify at least one data element, each data element is indicative of a respective medical parameter of a plurality of medical parameters, converting the at least one data element into at least one converted metadata value, analyzing the at least one converted metadata value with respect to another set of at least one converted metadata value obtained from at least one other medical UI presented on at least one other display of at least one other client terminal, to identify at least one baseline parameter, monitoring a plurality of frames captured from the video stream for detecting, according to a set of rules, a deviation from the at one baseline parameter, and generating instructions according to the deviation.

In a further implementation form of the first aspect, the medical data processing device is connected at least one of: (i) in-line between the client terminal and the display for capturing the video signals transmitted from the client terminal to the display, and (ii) to an outlet splitter port that outputs the video signals indicative of data presented on the display, and further comprising a component emulating a physical user interface for connecting to the physical input interface, for transmitting instructions emulating manual actions performed by a user manually reviewing the 3D anatomical image.

In a further implementation form of the first aspect, the 3D anatomical image is stored according to a format based on the DICOM® protocol, and wherein the display presents the 3D anatomical image within a PACS image viewer interface.

In a further implementation form of the first aspect, the medical imaging processing device further comprises instructions for: reconstructing the 3D anatomical image according to the formatted plurality of extracted 2D images slices and associated plurality of converted metadata values, and analyzing the reconstructed 3D image using computer aided diagnosis (CAD) code.

In a further implementation form of the first aspect, the plurality of converted metadata values includes metadata used for the 3D reconstruction, including at least one member selected from the group consisting of: 2D slice thickness, accumulated number of 2D slices, spacing between 2D slices, histogram window, imaging modality mode, serial number of anatomical imaging device that captured the imaging data presented as the plurality of 2D slices, version of software, study instance UID, series instance UID.

In a further implementation form of the first aspect, the instructions are for iteratively scrolling through parallel 2D frames of the 3D anatomical image for capturing the sequence of adapted 2D frames of the 3D anatomical image.

In a further implementation form of the first aspect, the 3D anatomical image is stored with a bit depth that is greater than a bit depth of the presented 2D frames of the 3D anatomical images, wherein the instructions are for adapting each respective 2D frame for capturing a plurality of variations of each respective 2D frame, and wherein the plurality of variations of each respective frame are processed into a single 2D image having bit depth equal to the bit depth of the stored 3D anatomical image.

In a further implementation form of the first aspect, the instructions are for adapting at least one of: contrast settings, range settings, and window settings, of each respective 2D frame for capturing the plurality of variations of each respective 2D frame.

In a further implementation form of the first aspect, the medical imaging processing device further comprises a network interface for transmitting the formatted plurality of images and associated plurality of converted metadata values over a network to a server computing the reconstruction of the 3D anatomical image.

In a further implementation form of the first aspect, the at least one metadata element is a sub-portion of the 2D frame denoting text, and the at least one converted metadata value comprises a text representation of the sub-portion of the 2D frame converted by an optical character recognition process.

In a further implementation form of the second aspect, the certain client terminal comprises a medical monitoring application monitoring a plurality of medical parameters of a patient, and the at least one other medical UI comprises an electronic medical record (EMR) application storing an EMR of the patient, wherein the at least one baseline parameter is identified according to a correlation between a patient identification presented within the medical UI of the medical monitor application and the patient identification presented within the medical UI of the EMR application.

In a further implementation form of the second aspect, the certain client terminal comprises a medical monitoring application monitoring a plurality of medical parameters of a patient, and the at least one other medical UI comprises an electronic medical record (EMR) application storing an EMR of the patient, wherein the at least one baseline parameter comprises a plurality of values for the plurality of medical parameters obtained from the EMR, wherein the plurality of frames are monitored to detect a deviation relative to the at least one baseline parameter of the plurality of medical parameters being monitored by the medical monitoring application.

In a further implementation form of the second aspect, the certain client terminal comprises a medical monitoring application monitoring a plurality of medical parameters of a patient, and the at least one other medical UI comprises an electronic medical record (EMR) application storing an EMR of the patient, wherein the at least one baseline parameter comprises a plurality of values for the plurality of medical parameters obtained from the EMR, wherein the plurality of frames are monitored to detect a deviation relative to the at least one baseline parameter of the plurality of medical parameters being monitored by the medical monitoring application.

In a further implementation form of the second aspect, the instructions comprise at least one of: storing an indication of the deviation in an EMR of the patient, transmitting an alert message for presentation on a screen of another computing device, and injecting an overlay alert for presentation over the certain medical UI presented on the certain display.

In a further implementation form of the second aspect, the medical processing device further comprising code for: capturing a plurality of historical frames presented within the certain medical GUI presented on the certain display, analyzing the plurality of frames to compute the at least one baseline parameter, monitoring a plurality of future frames presented on the certain display of the certain client terminal for detecting, according to the set of rules, the deviation from the at one baseline parameter.

In a further implementation form of the second aspect, the at least one data element comprises non-text data, and wherein the at least one converted value comprises text data representing the non-text data.

In a further implementation form of the second aspect, the non-text data is selected from the group consisting of: plot of a medical parameter as a function of time over a time interval, and region of an image representation of the respective frame.

In a further implementation form of the second aspect, the conversion from non-text data to text data is computed by at least one of: classifier trained on a training dataset of non-text data labeled with text data, and optical character recognition code that detects image representation of characters in the respective frame and converts the detected image representation to a text representation of the characters.

In a further implementation form of the second aspect, the medical processing device further comprising code for: monitoring at least the certain frame to identify manual entry of data by a user using the certain medical UI, analyzing the manual entry of data for detecting a deviation according to a set of rules, and generating instructions for presentation of an overlay over the certain medical UI associated with a location of the manual entry of data, indicative of at least one of: an error in the manual entry of data, and a recommendation for correction of the error.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF SPECIFIC EMBODIMENTS OF THE INVENTION

Figure 1:
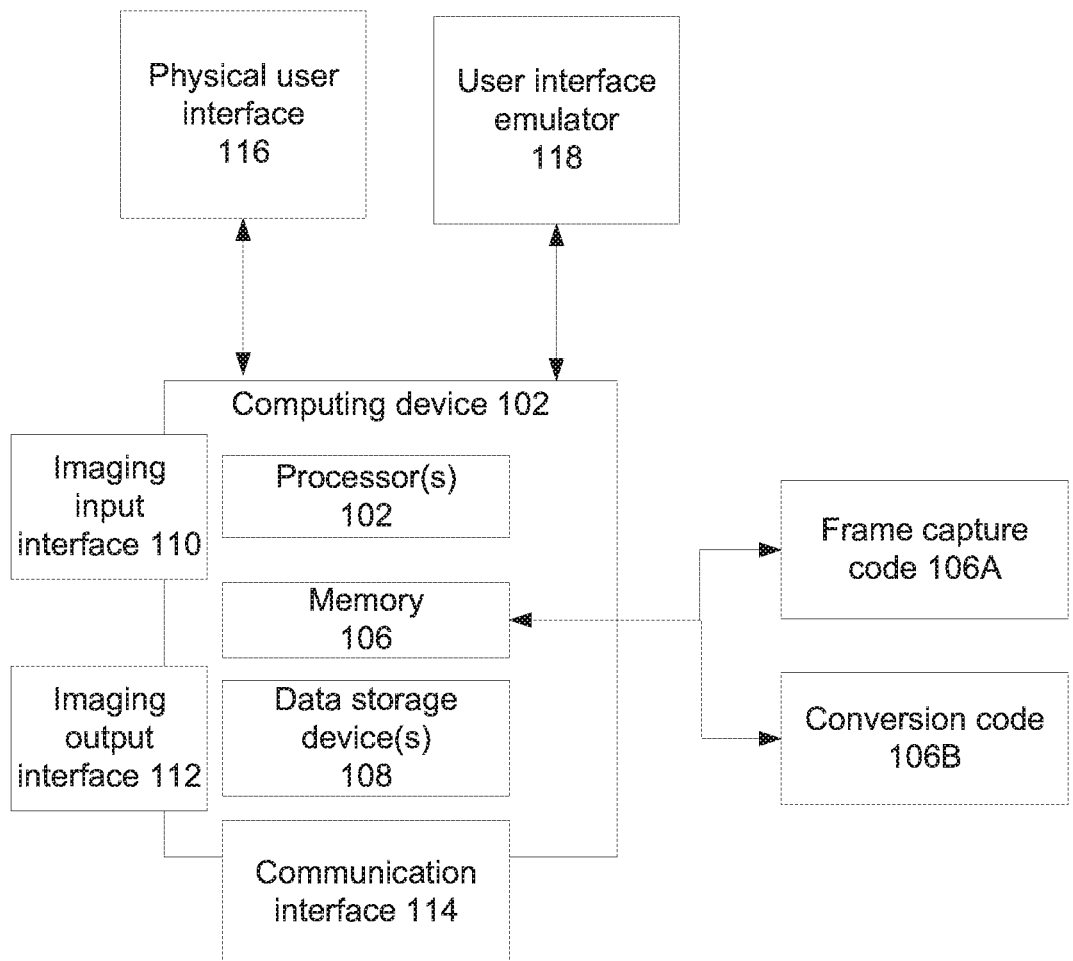
FIG. 1 is a block diagram of components of a computing device for capture and/or analysis of images presented within a user interface (UI) presented on a display of a client terminal, in accordance with some embodiments of the present invention.

The present invention, in some embodiments thereof, relates to image processing, more specifically, but not exclusively, to systems and methods for processing data extracted from frames captured from video signals of a display.

An aspect of some embodiments of the present invention relates to a device, a system, methods, and/or code instructions (e.g., stored in a memory and executable by one or more hardware processors) for computing 2D images and/or metadata values, captured from video signals of 2D frames of a 3D anatomical image presented on a display, for reconstruction of the 3D anatomical image. Instructions are generated for iterative adjustment of one or more presentation parameters of the 2D frames, for creating a sequence of adapted 2D frames of the 3D anatomical image. For example, the instructions are for scrolling through each one of the parallel 2D frames making up the 3D anatomical images, for example, each one of the slices of the CT scan. Each 2D frame is processed, by capturing the 2D frame from video signals, analyzing the captured 2D frame for extraction of a 2D image, analyzing the captured 2D frame to identify metadata, and converting the metadata into a converted metadata value. The set of extracted 2D images and associated converted metadata values are formatted for reconstruction of the 3D anatomical image.

The frames are grabbed from the video signals, which are obtained, for example, by an in-line (i.e., parallel) connection between the client terminal and the display, and/or from an outlet splitter port that outputs the video signals indicating the frames presented on the display, for example, from the port of the client terminal and/or display.

An aspect of some embodiments of the present invention relates to a device, a system, methods, and/or code instructions (e.g., stored in a memory and executable by one or more hardware processors) for generation of instructions based on data presented within multiple medical UIs presented on respective multiple displays of multiple client terminals. For each display presenting a respective medical UI, a respective frame of the video stream is captured. The certain frame is analyzed to identify one or more data elements indicative of medical parameter(s). The data element(s), which may be non-text based, for example, a graph (e.g., line, point, bar chart, pie chart, and the like) of the medical parameter over time, is converted into metadata value(s), optionally, a textual representation of the non-text data, for example, numerical value of the graph, stored as, for example, text comma separated values (CSV). The converted metadata values, obtained from multiple medical UIs presented on different screens, are analyzed to identify one or more baseline parameters. For example, values of medical parameters considered as normal for this patient (e.g., pulse oximeter measured oxygen saturation values in COPD patients ranging from 88-92% in comparison to 100% or close to 100% in healthy patients, and abnormal electrocardiography (ECG) waveforms which are due to long standing cardiac abnormalities in the patient, for example, ST segment depression resulting from a heart attack a few years ago). Patient ID may be compared to identify medical data (e.g., patient medical records) corresponding to the monitor UI. Multiple frames of one or more displays are monitored for detecting a deviation from the baseline parameter(s). Instructions may be generated when the deviation is detected, for example, storing an indication of the deviation in the matched electronic medical record (EMR) of the patient, for example, the value of the medical parameter measured by the medical monitor that led to the deviation. In another example, the generated instructions are for generating an alert indicative of the deviation, for example, sending the alert to a mobile device of a healthcare profession, injecting the alert into the video signals as an overlay over the medical UI, and pushing a pop-up window on a display of a monitoring station.

At least some implementations of systems, methods, and/or code instructions described herein relate to the technical problem of performing computer aided diagnosis (CAD) and/or other analysis processes (e.g., surgical simulation) using 3D medical images, for example, CT scan, MRI scan, and PET scan. The 3D medical images may be stored according to a medical protocol, for example, stored as DICOM® (Digital Imaging and Communications in Medicine) images in a picture archiving and communication system (PACS) server, and presented on a display within a PACS viewer application. Interfacing between the CAD application and the 3D images may be difficult and/or prone to error, in particular for DICOM® images. For example, approvals are needed, a capable IT department is required (which may not be available in all medical institutions), and implementing a new software solution using DICOM® images takes time. At least some implementations of systems, methods, and/or code instructions described herein provide a technical solution to the technical problem, by extracting 2D frames from 3D DICOM® images and extracting metadata from the 2D frames, and formatting the 2D frames and metadata for enabling 3D reconstruction of the 3D medical image. The reconstructed 3D medical image may be processed by other processing applications, for example, using CAD to detect tumors and/or other anatomical abnormalities, and/or used to perform surgical simulations. The 2D frames and metadata are extracted from the video stream of the display, without requiring installation at the endpoint client terminal presenting the images and/or installation at the medical equipment and/or installation at the PACS server. The 2D frames and metadata are extracted without requiring permission from providers.

As used herein, the term CAD application refers to an exemplary application of the 3D reconstruction. Other applications may be used, for example, simulation of surgery using the 3D reconstruction.

Standard approaches to using CAD applications (and/or other analysis applications) require integration with existing medical image applications and/or storage servers, for example, for obtaining the data from DICOM® images stored on a PACS server. Use of the actual DICOM® image is traditionally required in order to obtain the full amount of data stored in the DICOM® images, which is lost when presented on a display. For example, the DICOM® images presented on the display are defined by 8 bits, while the stored DICOM® images are defined using 12 bits. Therefore, to use the full 12 bits rather than the 8 bits, traditional CAD applications required the ability to use the DICOM® images directly, optionally obtained from the PACS server, which as described herein is technically difficult, slow, and/or complex.

However, Inventors discovered that the 2D images extracted from video signals of frames of the 3D anatomical image provide sufficient data for accurate 3D reconstruction of the 3D anatomical image. Even through the video signals contain less information than the stored 3D anatomical image, additional data may be recovered by at least some implementations of systems, methods, and/or code instructions described herein. Additional data is obtained by the automatic generation of instructions that emulate manual user input, for iterating through different combinations of presentation parameters. Each 2D frame is presented multiple times, each time with a different combination of presentation parameters, for example, different CT settings (e.g., CT windows). The multiple presentations of each frame, which each have relatively low amount of data, are formatted (e.g., combined, aggregated) into a single frame with a high amount of data corresponding to the amount of data (i.e., bit depth) in the original 3D DICOM® image. Moreover, the metadata extracted from the 2D frames is used to reconstruct the 3D anatomical image, providing further accuracy of the reconstruction in comparison to the original DICOM® image. Alternatively, in some applications, the full bit depth of the original stored 3D anatomical image is not required. For example, for processing the reconstructed 3D anatomical by a CAD application, a smaller bit depth than the full bit depth of the original stored 3D anatomical image may be sufficient.

At least some implementations of systems, methods, and/or code instructions described herein relate to the technical problem of extracting data from an existing software system, without modifying the existing software, or adding software to it. Reasons for avoiding modification of the existing software system include, for example, because the software vendor does not support such modifications, the software vendor may no longer exist, the modification may present difficult commercial terms, and/or due to the long time and/or complexity such software modifications may require.

At least some implementations of systems, methods, and/or code instructions described herein perform the extraction from frames captured from the video signals, in contrast to performing a screen capture operation. The video signals are sent by the client terminal to the display. The video signals may be obtained, for example, by being intercepted by an in-line (i.e., parallel) connection between the client terminal and the display. In another example, the video signals are obtained from an outlet splitter port (e.g., of the client terminal and/or display) that provides an output of the video signals, without affecting the frames presented on the display. Capturing frames from the video signals may be performed without impacting performance of the client terminal, without affecting operation of other applications installed on the client terminal, without installation of code on the client terminal, and/or without using processing resources and/or memory resources and/or data storage resources of the client terminal. In contrast, performing a screen capture operation directly impacts the client terminal, by requiring installation of code on the client terminal, using processing and/or memory and/or data storage resources of the client terminal, which may affect performance of the client terminal and/or affect operation of other applications installed on the client terminal.

At least some implementations of systems, methods, and/or code instructions described herein improve the technology of extracting data from one software system for use by another software system. The improvement is at least that the extraction is performed without modifying the software system from which data is being extracted, and/or without adding addition code for execution by the computing device that executes the software system from which data is being extracted. The improvement is at least that the extraction of data from the software system is performed without using processing resource and/or data storage resources (e.g., memory) of the computing device executing the software system from which data is being extracted.

The improvement provided by at least some implementations of systems, methods, and/or code instructions described herein is in contrast to existing generic automated processes, for example, Robotic Process Automation (RPA), and Website Scraping. Such existing processes provide mere automation of manual work as done by a human user. RPA is a more general approach for generic software, and Website Scraping is focused on websites. Any extraction of data from a screen is simply done automatically according to the manual process a human follows, by "reading" information. Any automated entry of information is simply done according to the manual process a human follows, by "typing". RPAs are especially useful for performing "Swivel Chair" work, where data from one system is copied to another system. For example, to transfer data from one database to another database, the automated processes would simply copy data from defined fields of one database, and enter it into another field of the other database. For example, the home address and phone number of multiple patients and/or clients may be automatically copied from one database to another, rather than having a human manually perform the task.

At least some implementations of systems, methods, and/or code instructions described herein do not automate manual tasks in the same way they had been previously carried out, but create a new automated process based on data extracted from the display, where the new automated process includes (alone or in combination) new features that have never been performed before and/or features that have no manual counterpart, for example, creating a new set of formatted 2D medical images including extracted parameters for rendering a 3D model and/or for further processing of the 3D model, and/or converting non-text data (e.g., graphs, tables, images) into a text value denoting the non-text data, and/or analyzing extracted data (optionally in correlation to data extracted from other displays displaying other systems) for identifying a baseline value(s), and/or correlating data originating from different software programs presented on different screens. For example, correlating the slice number and filename presented by a PACS image viewer, with the actual image of the slice, allowing reconstruction of the 3D scan and DICOM® folder of the whole scan with the various slices in order. In another example, the ICU monitor data collected by a monitoring device is correlated with the EMR record of a patient using the same patient id (e.g., number, name) presented on the display of the ICU monitor and stored in the EMR system. In another example, the PACS viewer, which is presenting a DICOM® image (e.g., CT scan) stored in a PACS server, may be adapted to display the same image/2D slice in multiple different contrast range/setting parameters for recovering the full DICOM® CT readings which may be 12 bit or more, in comparison to the screen display which may be 8 bit.

It is noted that optical character recognition (OCR) performed on data extracted from digital displays to identify characters has a very high level of reliability, in comparison to OCR performed on a scanned paper. For a known font, extraction of text from an image presented on a display may be as reliable as reading the text stored on a data storage device.

Moreover, such existing generic automated processes are implemented by a software client that runs on the endpoint that controls the display from which data is obtained and to which data is being added. Such approach has several disadvantages, for example: (i) The additional installed client code cannot work for software systems where the endpoint cannot support the client software (e.g. incompatible O/S and/or not an open O/S), and/or the vendor of the software running on the endpoint may not approve the installation of such client software, for example, due to performance, reliability and/or security concerns. For example, when the endpoint is running an industrial control software, no other software may be installed on it without the vendor consent, which may not be possible to obtain. (ii) Installation of the software code on the endpoint may consume a significant portion of the endpoint CPU, memory resources and/or data storage resources, which degrade computational performance of other processes executed by the endpoint. (iii) Computationally intensive processes (e.g., deep neural networks and/or other machine learning processes) cannot be executed by the endpoint, since such computationally intensive processes would use a significant portion of the resources of the endpoint resulting in drastic decline in performance for other executing processes, and/or the hardware of the endpoint is not designed to handle such processes, especially in real time. (iv) Since generic automated processes are designed to be integrated with existing software, the generic automated processes require continual updating, installation, IT consent and support, in order to keep up with updates of the existing software. (v) Generic automated processes cannot be integrated with legacy systems and/or old computer equipment, for example, since such automated processes are designed to run on recent operating systems and/or recently introduced hardware. (vi) Generic automated processes cannot be integrated with specialized equipment, for example, PACS/VNA (vendor neutral archive), EMR, RIS (Research Information Systems), and medical imaging devices (e.g., CT, MRI, X-ray, US), OT HMI (human machine interface), PLC/SCADA (supervisory control and data acquisition) equipment. (vii) Generic automated processes cannot be integrated with mission critical systems, such as those found in hospitals and/or plants. (viii) Data is only extracted from static screens. (ix) Limited to simple extraction of data, such as text. (x) Limited to simple entry of data into another system, such as text.

At least some implementations of systems, methods, and/or code instructions described herein address the above challenges, providing an improvement over traditional RPA type processes. For example: (i) The computing device described herein is connected (e.g., in-line and/or via splitter), and processes the video stream (and/or other instructions) being displayed on the display by capturing frames of the video stream, which is independent of the underlying operating system, and/or vendor of the software. (ii) The computing device has its own dedicated processors, memory, and/or data storage devices, and does not rely on and/or utilize processing resources of the endpoint client terminal. (iii) The computing device may include hardware resources designed to perform computationally intensive tasks, optionally in real time. (iv) No integration with code running on the endpoint is required. (v) Integration with legacy systems and/or old computer equipment is easily performed. (vi) Integration with specialized equipment is easily performed. (vii) Integration with mission critical systems is performed with risk of affecting performance of the mission critical system and/or without risk of tampering with the mission critical system. (viii) Data may be extracted from dynamic screens. (ix) Non-text data, such as graphs, tables, and images, may be extracted and/or processed, for example, to compute text-based values. (x) Complex new data structures may be created, for processing by another system, for example, a set of 2D images and related data for rendering into a 3D model by code.

In contrast, at least some implementations of systems, methods, and/or code instructions described herein provide a technical solution, in extracting data presented on displays and/or processing the extracted data without installation of client code on the endpoint. The extraction and/or processing of the data is done externally to the display and/or the client terminal sending instructions for the display, by a dedicated computing device having its own processing resources, memory resources, and/or data storage resources. No direct interface and/or integration with existing software systems is necessary. The extraction and/or processing of the data is performed by intercepting signals and/or instructions for presentation on the display before arrival at the display, and/or via a split of the current presentation of the display (e.g., via an output port of the display and/or the client terminal). Moreover, at least in the case of connection via the splitter, failure or malfunction of the computing device does not affect operation of the software system, display, and endpoint.

The technical solution to the described technical problem provided by at least some implementations of systems, methods, and/or code instructions described herein does not require vendor approval, has no effect on the existing endpoint performance and/or endpoint resources (since the processing resources and/or memory of the endpoint are not used). Computationally expensive processing may be performed on the data presented on the display (e.g., by neural networks and/or other machine learning processes) by the dedicated hardware and/or software, optionally in real time. Graphics and/or images may be extracted and/or processed, optionally in real time, by the dedicated hardware and/or software.

At least some implementations of systems, methods, and/or code instructions described herein transform a standard display of a client terminal into a smart display without tampering with the original display and/or without integration of additional client code into the client terminal, by using the computing device described herein. Standard displays may include, for example, generic monitors, displays integrated into the client terminal, displays external to the client terminal, and customized displays, for example, designed to present specific data. The smart display may be created by injecting a graphical overlay into the standard display, based on an analysis of data presented on the standard display, as described herein. Exemplary injected graphical overlays include, for example, identifying fields with invalid values and injecting a graphical overlay over the fields indicative of the invalid values (e.g., inverted color, highlight, and/or comment). In another example, the injected graphical overlay includes instructions for a user to perform based on the current presented content, for example, highlighting empty fields in a form that require data, and/or marking the next data section. In yet another example, the injected graphical overlay is based on monitoring multiple frames captured over a time interval, analyzing the frames to detect an activity, and generating instructions accordingly, for example, when a certain UI segment that is open for a long time with no action taken is identified, instructions may be generated and presented as an overlay indicating that the user needs to take action.

The technical problem addressed by at least some implementations of systems, methods, and/or code instructions described herein is unique to the technological context of software systems presented on a display within a user interface, which arose due to improvements in technology of software systems and devices, and does not have a counterpart in the old physical world. The problem arose precisely due to the fast evolving world of software, which led to fast developments of new versions of software, and/or specific formats to be followed for implementing the software, which led to the difficulty of integration of new code into existing software platforms.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
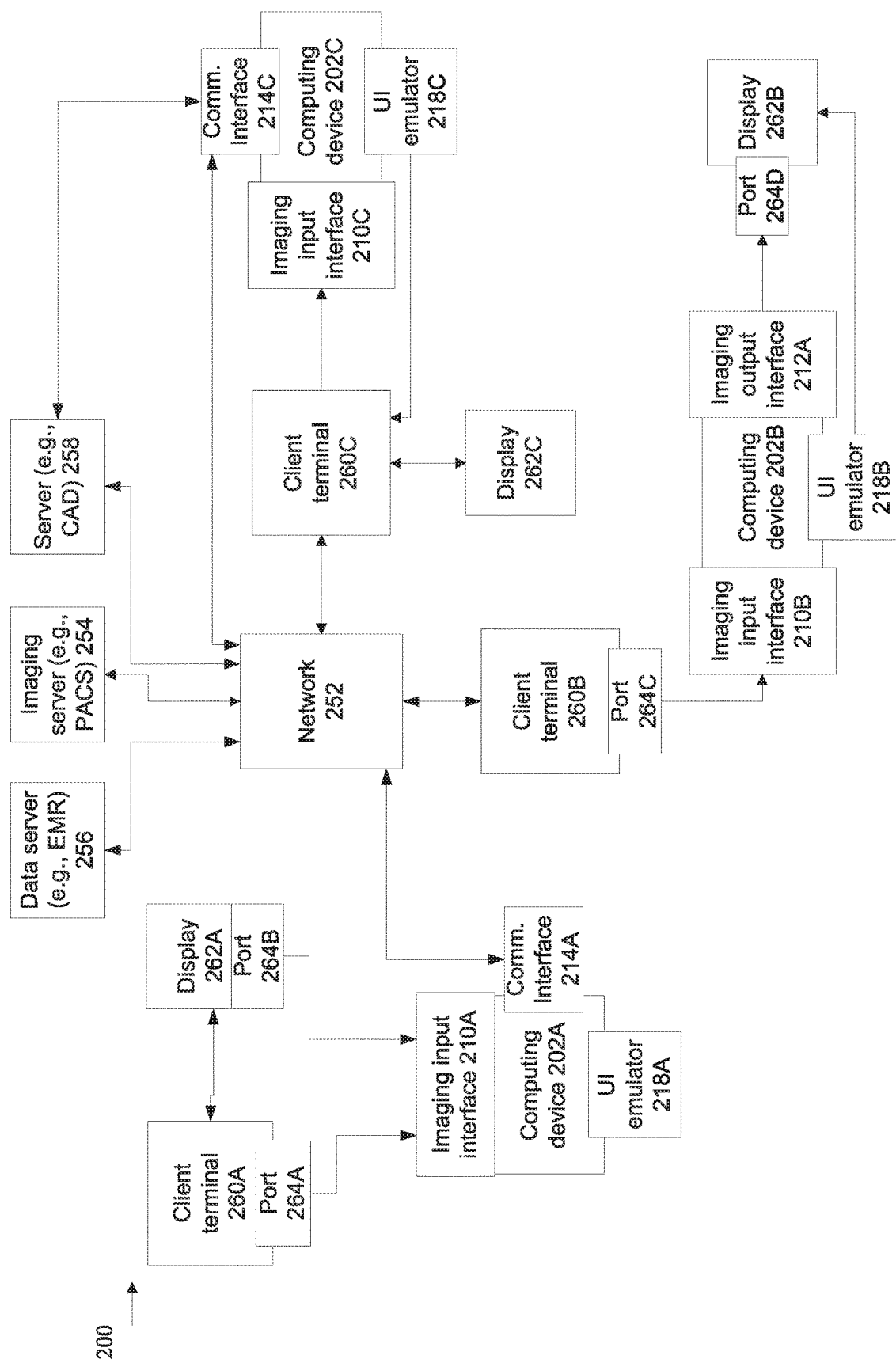
FIG. 2 is a block diagram of components of a system including the computing device of FIG. 1, depicting exemplary architectures for connecting the computing device to various components, in accordance with some embodiments of the present invention.
Figure 3:
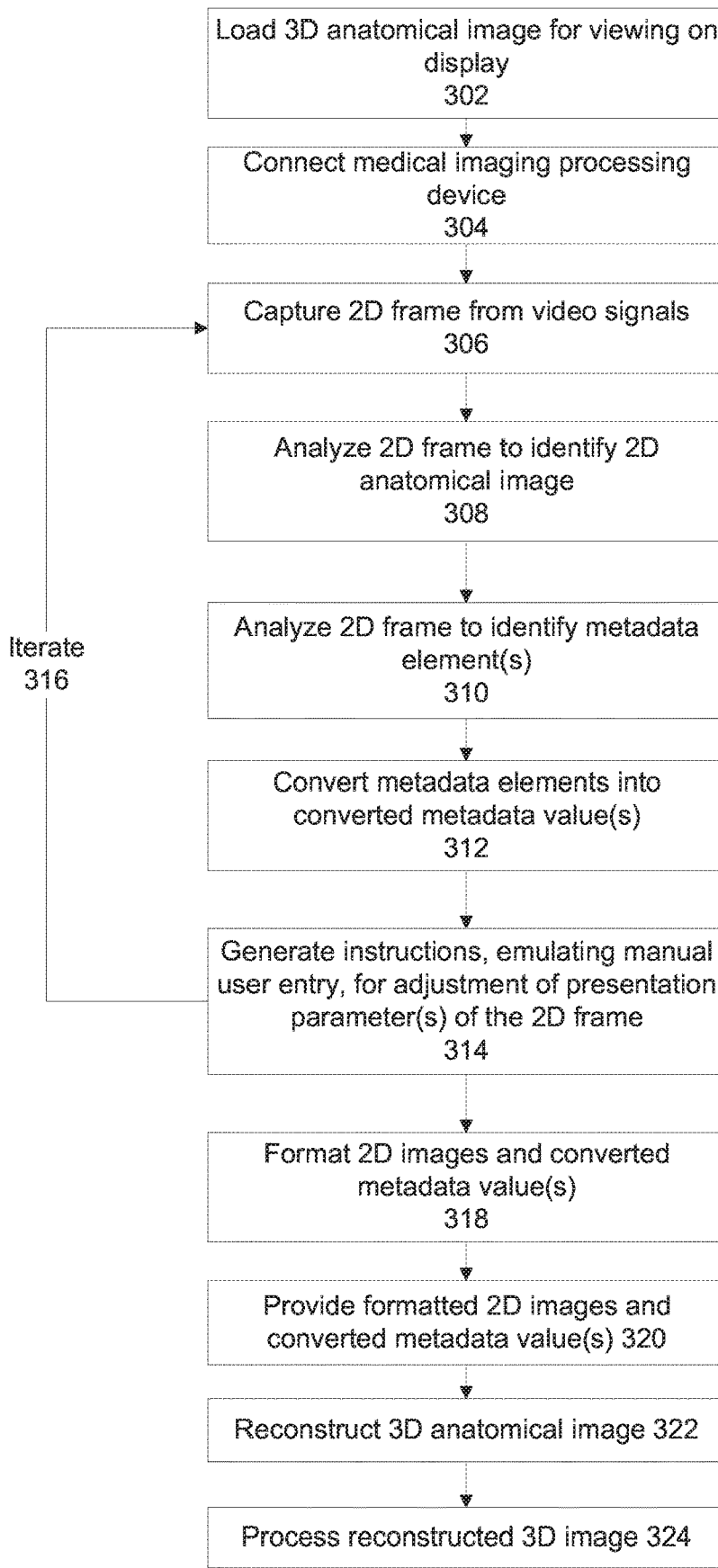
FIG. 3 is a flowchart of a process for generating data for reconstruction of a 3D anatomical image from 2D frames captured from video signals for presentation on a display of a client terminal, in accordance with some embodiments of the present invention.
Figure 4:
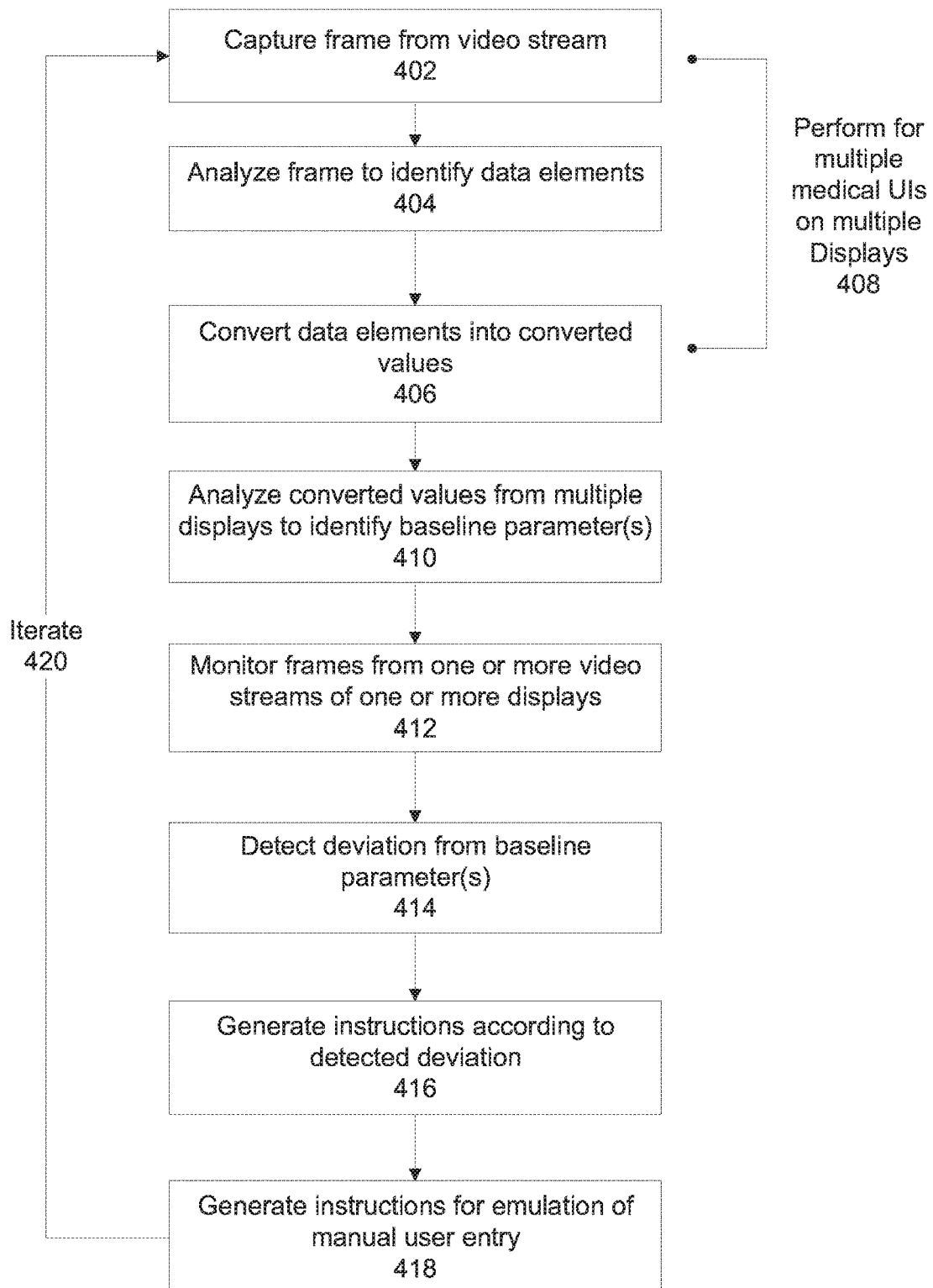
FIG. 4 is a flowchart of a method for generation of instructions based on data presented within multiple medical UIs presented on multiple displays of multiple client terminals, in accordance with some embodiments of the present invention.

Reference is now made to FIG. 1, which is a block diagram of components of a computing device 102 (also referred to herein as medical imaging processing device and/or medical data processing device) for capture and/or analysis of images presented within a user interface (UI) presented on a display of a client terminal, in accordance with some embodiments of the present invention. Reference is also made to FIG. 2, which is a block diagram of components of a system 200 including computing device 102 of FIG. 1, depicting exemplary architectures for connecting computing device 102 (i.e., the medical imaging processing device and/or medical data processing device) to various components, in accordance with some embodiments of the present invention. Reference is also made to FIG. 3, which is a flowchart of a process for generating data for reconstruction of a 3D anatomical image from 2D frames captured from video signals for presentation on a display of a client terminal, in accordance with some embodiments of the present invention. Reference is now made to FIG. 4, which is a flowchart of a method for generation of instructions based on data presented within multiple medical Uls presented on multiple displays of multiple client terminals, in accordance with some embodiments of the present invention. The method describe with reference to FIGS. 3-4 may be implemented by computing device 102 described with reference to FIG. 1, and/or by components of system 200 described with reference to FIG. 2.

Computing device 102 is implemented as an external and/or standalone and/or independent hardware component, which is external and/or independent of client terminals, displays, and/or servers, as described herein. For example, in contrast to standard processes, computing device 102 is not comprises of code installed on the client terminal(s) and/or server(s), executed by processor(s) of the client terminals(s) and/or servers(s), using memory of the client terminal(s) and/or server(s), that analyzes the images presented on the displays of the server(s) and/or client terminal(s). Rather, computing device 102 is connected to client terminals(s) and/or servers, for intercepting instructions and/or signals for presentation of the images on the display, and/or receives an indication of the image(s) presented on the display via a port of the client terminal and/or server and/or display, for example, where the port acts as a splitter that outputs the same (or a copy of) the signals and/or instructions used for generating the image(s) on the display. Moreover, computing device 102 uses its own dedicated processor(s) 104 resources, and/or memory 106 resources, and/or optionally data storage device resource(s) 108, rather than using the processor(s) and/or memory and/or optionally data storage device resources of the server(s) and/or client terminal(s) associated with the display(s) from which the images are captured. It is noted that computing device 102 may be implemented as an existing device on which code is loaded for execution of the features described herein (e.g., capturing images, analyzing the images), however the existing device is independent and/or external and/or standalone with respect to the server(s) and/or client terminal(s) associated with the display(s) from which the images are captured.

Computing device 102 may be implemented as, for example, a dedicated device including dedicated hardware and/or software and/or firmware, another computing device, another server, a virtual machine running on another physical platform, a mobile device (e.g., smartphone, tablet, laptop, wearable computer, glasses computer, watch computer), a desktop computer, and a computing cloud.

Computing device 102 may include one or more user interface emulators 118, which are designed to attach to a client terminal and/or display and emulate manual user input, for example, emulate entry of a keyboard, emulate entry by a touchscreen, and emulate entry via a mouse. User interface emulators 118 may connect to client and/or display, optionally using standard physical connection interfaces used by standard user interfaces, for example, via a USB port and/or wireless connection (e.g., wireless keyboard interface). Computing device 102 generates instructions for emulating manual entry on the display of the client terminal via user interface emulator 118, for example, emulating manual user keystrokes and/or mouse actions to sequentially scroll through 2D slices of a CT scan.

Hardware processor(s) 104 may be implemented, for example, as a central processing unit(s) (CPU), a graphics processing unit(s) (GPU), field programmable gate array(s) (FPGA), digital signal processor(s) (DSP), application specific integrated circuit(s) (ASIC), and processors designed for artificial intelligence (AI), deep network processing, and/or machine learning application. For example, an AI chip+system on a chip (SOC) combination, for example, ARM+CEVA, Intel I3+VPU). Processor(s) 104 may include one or more processors (homogenous or heterogeneous), which may be arranged for parallel processing, as clusters and/or as one or more multi core processing units.

Memory 106 (also referred to herein as a program store, and/or data storage device) stores code instruction for execution by hardware processor(s) 104, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 106 stores code instructions that perform one or more of the features described with reference to FIGS. 3-4, for example, frame capture code 106A for capturing frames of images for presentation on the display of the client terminal and/or serer, and/or conversion code 106B for converting data elements(s) extracted from the captured images into converted values, as described herein It is noted that frame capture code 106A and/or conversion code 106B may be implemented in hardware, for example, as customized chips.

Optionally, frame capture code 106A is designed to convert frames captured from video signals into digital format.

It is noted that features described with reference to FIGS. 3-4 may be performed by two or more computing devices 102, which may be in communication with one another (e.g., over a network). For example, some features are implemented by one computing device 102, and other features are implemented by another computing device 102. All computing devices 102 are external, and/or standalone, and/or independent, with respect to client terminals and/or servers described herein.

Computing device 102 includes one or more imaging input interfaces 110 for receiving instructions and/or signals of image(s) for presentation on a display of a client terminal and/or server. Computing device 102 may include one or more imaging output interfaces 112 for outputting instructions and/or signals of image(s) for presentation on the display of the client terminal and/or server, for example, the unaltered original signals and/or instructions received via imaging input interface(s) 110 (e.g., when computing device 102) is installed in-line (i.e., in series) between the client terminal and/or server and the display, for intercepting the signals and/or instructions), and/or for injecting a graphical overlay for presentation over the original image, as described herein.

Computing device 102 may include one or more communication interface(s) 114 for communicating with other client terminals and/or servers, directly and/or over a network.

Imaging input interface(s) 110 and/or imaging output interface(s) 112 and/or communication interface(s) 114 may be implemented, for example, as a wire connection (e.g., physical port), a wireless connection (e.g., antenna), a local bus, a port for connection of a data storage device, a network interface card, a wireless interface to connect to a wireless network, a physical interface for connecting to a cable for network connectivity, a virtual interface implemented in software, network communication software providing higher layers of network connectivity, and other physical interface implementations, and/or virtual interfaces (e.g., software interface, virtual private network (VPN) connection, application programming interface (API), software development kit (SDK)), and combinations of the aforementioned.

Computing device 104 may include data storage device(s) 108 for storing data, for example, sets of rules for determining deviation from baseline, storing the digital representation of the frames captured from the video signals, storing segmentation code for extraction of images from the frames, and storage of other code and/or data according to implementation. Data storage device(s) 108 may be implemented as, for example, a memory, a local hard-drive, a removable storage device, an optical disk, a storage device, and/or as a remote server and/or computing cloud (e.g., accessed over a network, optionally via communication interface 114).

Computing device 102 may include and/or be in communication with and/or include an interface for communication with: one or more user interfaces 116. User interface(s) 116 may provide an indication of active capture of image(s) and/or active processing of the captured image(s), may include a mechanism for the user to enter data (e.g., define a set of rules for capturing data elements from the image(s) such as defining which portion of the image(s) to analyze and/or defining how CT images are to be adjusted for visualization), and/or a mechanism for the user to view data (e.g., view the converted values obtained from the captured image). Exemplary user interfaces 226 include, for example, one or more of, a flashing light (e.g., LED), a touchscreen, a display, a keyboard, a mouse, and voice activated software using speakers and microphone.

Reference is now made to FIG. 2, which depicts various exemplary architectures for connecting computing devices 202A-C (corresponding to computing device 102 described with reference to FIG. 1), to components, for example, to a network 252, an imaging server (e.g., PACS server) 254, a data server 256 (e.g., EMR server), a server 258 (e.g., hosting code for analyzing the data outputted by the computing device, for example, a CAD application), and client terminals 260A-C (e.g., ECG monitoring device, kiosk, pulse oximeter, ventilation machine, heart and lung machine, kidney dialysis monitoring device, radiology workstation, PACS viewing station, medical imaging machines (e.g., CT, MRI, X-ray, ultrasound), endoscope, microscope, catheterization lab workstation, standard computer running viewing and/or monitoring code, standard mobile device running viewing and/or monitoring code, standard server running viewing and/or monitoring code.

Imaging server 254 stores anatomical images, optionally 2D and/or 3D and/or 4D anatomical images, optionally according to the DICOM® standard. Imaging server 254 may be implemented as a PACS server.

Each client terminal 260A-C is associated with a respective display 262A-C, which may be an external and/or standalone and/or independent display connected to the respective client terminal, for example, by a cable (e.g., HDMI, VGA, SDI, DVI) and/or by a wireless connection. Alternatively, displays 262A-C may be implemented as an integrated component integrated within the respective client terminal 260A-C, for example, a screen of a mobile device, a screen of a laptop, and/or a monitor built in to the monitoring device (e.g., display of a pulse oximeter).

Each client terminal 260A-C is optionally associated with a respective UI emulator 218A-C, which is connected to a UI interface of respective client terminals and/or displays. UI emulator 218A-C emulates manual actions entered by a user using a user interface (e.g., keyboard, mouse) for adapting the presentation on the display and/or entering data via the display, as described herein.

Network 252 may be implemented, for example, as one or more of: a wire based network (e.g., Ethernet), a wireless based network, the internet, a local area network, a wide area network, a virtual private network, a virtual network, a cellular network, a short range wireless network, a mesh network, and an ad-hoc network. Network 252 may be implemented using one or more protocols and/or network architectures.

Several exemplary architectures for connecting the computer device to the client terminal and/or server are now described. It is noted that other architectures may be used, for example, combinations of the described architectures. Computing devices 202A-C may receive the input via imaging input interface 210A-C corresponding to imaging input interface 110 of FIG. 1.

In one exemplary architecture, client device 260A is a standalone device, optionally unconnected to network 252 (in some implementations connected to network 252), for example, a pulse oximeter, a ventilation machine, and an ECG monitor. Computing device 202A receives, via interface 210A, input of the image presented on display 262A of client terminal 260A (which may be integrated with client terminal 260A and/or connected via cable and/or a wireless connection). The instructions for presentation of the image and/or signals of the presented image may be outputted by an output port 264B of display 262A and/or output port 264A of client terminal 260A, for example, an HDMI and/or VGA cable. Computing device 202A may communicate with any of server(s) 254, 256, 258 via network 252, and/or directly, via communication interface 214A, which corresponds to communication interface 114 described with reference to FIG. 1. It is noted that UI emulator 218A is not necessarily connected to a UI input port of client terminal 260A and/or display 262A. Such architecture may be used, for example, to extract data from displays of standalone devices and/or network connected devices, for example as described with reference to FIG. 4. The extracted data may be used to update patient medical records, for example, creating a log of the patient ventilation values, and/or creating alerts of detected abnormal values for taking action by relevant healthcare personnel.

In another exemplary architecture, computing device 202B is connected in-line (e.g., in series) between client terminal 260B and display 262B. For example, a cable is connected from output port 264C of client terminal 260B to input imaging interface 210B, and another cable is connected from output imaging interface 212B (corresponding to output imaging interface 112 of FIG. 1) to input port 264D of display 262B. Computing device 202B may or may not be connected to network 252 and/or servers 254, 256, 258 via a communication interface. As shown, UI emulator 218B is connected to a UI input port of display 262B for example for adapting the presentation of the images on display 262B, where the adapted images are captured by computing device 202B. It is noted that the UI emulator may be connected to the UI input port of client terminal 260B, and/or UI emulator 218B may not be connected at all in this architecture. Such architecture may be used, for example, to inject enhanced graphical overlays over the original images, for example as described with reference to FIG. 4.

In yet another exemplary architecture, client terminal 260C is connected to servers 254 and/or 256, optionally via network 252. Display 262C is connected to client terminal 260C and/or integrated therein. Computing device 202C is connected to client terminal 260C and/or display 262C via input imaging interface 210C. Computing device 202C is connected to servers 254 and/or 256 and/or 258, directly and/or over network 252, via communication interface 214C. UI emulator 218C is connected to a UI input port of client terminal 260C for automatically adapted presentation parameters of the frames presented on display 262C. Such architecture may be used, for example, to capture anatomical images obtained from a PACS server and presented on a radiology workstation, for example as described with reference to FIG. 3. The captured images may be processed and provided for 3D reconstruction and/or analysis, for example, by a CAD server.

Referring now back to FIG. 3, at 302, an anatomical image, optionally a 3D anatomical image is loaded for viewing, for example, by a PACS viewer application presented on a display of a client terminal. The 3D anatomical image may be stored in an imaging server, for example, a PACS server. The 3D anatomical image may be formatted according to a defined medical imaging standard, for example, DICOM®.

It is noted that the process described with reference to FIG. 3 may be implemented for a single 2D image (e.g., x-ray), and/or for 4D images.

At 304, the medical imaging processing device (i.e., computing device described with reference to FIG. 1 and/or FIG. 2) is connected for obtaining video signals.

The medical processing device may be connected, for example: (i) in-line between the client terminal and the display for capturing the video signals transmitted from the client terminal to the display, and (ii) to an outlet splitter port (of the client terminal and/or display) that outputs the video signals indicative of data presented on the display.

A component emulating a physical user interface (e.g., corresponding to element 118 described with reference to FIG. 1, and/or as described with reference to FIG. 2) may be connected to the client terminal and/or display. The component emulates a user interface designed for manual data entry by a user, for example, keyboard and/or mouse. The component transmits instructions automatically generated by the medical processing device to the client terminal (and/or display). The automatically generated instructions emulate manual actions performed by a user manually reviewing the 3D anatomical image.

At 306, the 2D frame currently presented on the display of the client terminal (also referred to as respective 2D frame) is captured from video signals. The frame may be captured, for example, by frame capture code 106A of computing device 102. Frame capture code 106A may be implanted as code instructions stored in memory 106 executable by processor(s) 104, and/or as a hardware component (e.g., customized chip). The video signals may be converted into digital format, for a digital representation of the 2D frame.

Processing of the video stream may be performed in real-time. Alternatively or additionally, processing of the video stream may be performed offline, from a stored video stream, for example, depending on the application, complexity, costs, and/or installation scenario. For example, compliance verification may be performed offline. Monitoring of medical devices monitoring a patient may be performed in real time.

At 308, the captured current 2D frame (also referred to as respective 2D frame) may be analyzed for identification of a 2D anatomical image component. The 2D anatomical image component is extracted from the captured 2D frame. For example, when CT slices are presented on the display within the PACS image viewer, additional parts of the frame, which are not part of the 2D slices are also presented on the display, for example, metadata associated with the anatomical image, background/desktop/other applications (i.e., when the PACS image viewer is open within a window and not on the entire screen).

The part of the 2D frame that includes the 2D anatomical mage component may be identified, for example, based on a set of rules that define the 2D anatomical image (e.g., according to location on the display, according to pixel values), based on manual settings defined by a user (e.g., application engineer installing the computing device and/or based on manufacturer settings), based on analysis code that detects images and/or other visual information of values, and/or based on trained classifier and/or segmentation code that segments the 2D anatomical image from the 2D frame according to detected boundaries.

The segmented images may be stored, for example, in an optimally compressed format for the target application.

At 310, the captured current 2D frame (also referred to as respective 2D frame) is analyzed to identify one or more metadata elements, optionally DICOM® metadata.

The metadata of the 2D frame may be identified, for example, based on a set of rules that define the location and/or appearance of the metadata, based on manual settings defined by a user (e.g., application engineer installing the computing device and/or based on manufacturer settings), and/or based on trained classifier and/or segmentation code that segments the metadata from the 2D frame.

At 312, the metadata element(s) are converted into converted metadata value(s).

Optionally, the metadata element(s) is an image sub-portion of the 2D frame. The image sub-portion may denote text, but is currently part of the image sub-portion. The image sub-portion may be extracted and/or segmented. Alternatively, the entire 2D frame is analyzed. Text may be extracted from the image sub-portion (and/or from the entire 2D frame), for example, by an optical character recognition (OCR) process. The converted metadata value(s) may be stored as a text.

Exemplary text includes alphanumeric characters, numbers, and/or symbols. Characters may be in English and/or other languages.

At least some of the converted metadata value(s) are used for guiding the 3D reconstructions from the set of 2D images.

Exemplary converted metadata value(s) (and/or values computed from the converted metadata values and/or values computed from an analysis of the captured 2D images) includes one or more of: 2D slice thickness, accumulated number of 2D slices, spacing between 2D slices, histogram window, imaging modality mode, serial number of anatomical imaging device that captured the 3D anatomical image presented as 2D slice(s), version of software, study instance unique identifier (UID), series instance UID.

At 314, instructions are generated, emulating manual user entry using a user interface. The instructions are generated for adjustment of one or more presentation parameter of the current 2D frame of the 3D anatomical image presented on the display. Alternatively, a user manually generates the instructions for adjustment of the presentation parameter(s) via a physical user interface, for example, keyboard, and mouse.

Optionally, the instructions are generated for creating a sequence of adapted 2D frames of the 3D anatomical image.

For example, the instructions are for iteratively scrolling through parallel 2D frames of the 3D anatomical image. For example, the instructions emulate a user turning the scroll wheel on the mouse to advance by one 2D frame (e.g., of the set of parallel 2D frames of a CT image). In another example, the instructions emulate a user pressing an arrow key on the keyboard to advance by one 2D frame.

Alternatively or additionally, the instructions are generated for adapting one or more presentation parameters of the current 2D frame, where the next 2D frame is the same depicted anatomy with adjustment of the presentation parameter. The current 2D frame is maintained, and not advanced to the next frame. Exemplary the instructions are for adapting one or more of: contrast settings, range settings, and window settings.

At 316, acts 306-314 are iterated.

Optionally, the iterations are performed for the same current 2D frame, for capturing multiple instances of the same 2D frame, where each instance of the 2D frame has different presentation parameters. The captured variations of each respective 2D frame are processed into a single 2D image. The data combined from the multiple variations increases the data (e.g., bit depth) of the single 2D image, optionally to correlate with the data (e.g., bit depth) stored in the original 3D anatomical image (e.g., DICOM® image). For example, each variation of the single 2D image has 8 bits. The multiple variations are combined into a single image having 12 bits, which may correspond to the data stored in the original 3D anatomical image. It is noted that this feature may performed for 2D images, such as x-rays. The iterations may be performed, for example, by generating instructions for multiple adaptations of each 2D frame, and then scrolling to the next 2D frame. Each 2D frame is adapted through the set of adaptations before moving to the next 2D frame. A single pass through all 2D frames may be made with multiple adaptations of each 2D frame. In another implementation, all 2D frames are scrolled through using the same adapted settings. Once all 2D frames are captured, instructions for adaptation are generated, and another iteration through all 2D frames is made. Multiple iterations of the 2D frames are made, each iteration for another adaptation.

Optionally, during the iterations, the instructions are generated for capturing enough data for reconstructing the bit depth of the original 3D anatomical image (e.g., the scored DICOM® image). In such implementation, the bit depth of the presented 2D frames is less than the bit depth of the stored 3D anatomical images, for example, 2D frames are presented with 8 bits, and the 3D anatomical images are stored with 11 or 12 bits or other values. The instructions and iterations are performed to generate enough data to reconstruct the original bit depth. Alternatively, the instructions and iterations are generated to capture data sufficient for process of the reconstructed 3D image by another application, for example, CAD. The application may be able to process images with less bit depth than the original stored 3D anatomical images. The reconstructed 3D anatomical images may be further pre-processed, for example, sharpening, histogram stretch, and/or other pre-processing as required by the application.

Alternatively or additionally, the iterations are performed for scrolling through the 2D frames of the 3D anatomical image, optionally for all 2D frames (or subset thereof, for example, to extract a certain organ and/or body part from a larger scan). A sequence of 2D images is captured for the 3D anatomical image.

At 318, the extracted 2D images and associated converted metadata values are formatted for reconstruction of the 3D anatomical image. The formatting may be defined, for example, according to the CAD application being used, and/or according to an open standard.

At 320, the formatted 2D images and associated converted metadata values are provided, for example, stored locally in the computing device, and/or transmitted to another device and/or transmitted over the network, for example, to a server hosting the code for reconstruction of the 3D anatomical image and/or for storage.

The formatted 2D images and associated converted metadata values may be transmitted directly to a server and/or over the network, for example, via the communication interface (e.g., network interface) of the computing device.

At 322, the 3D anatomical image may be reconstructed according to the formatted extracted 2D images slices and optionally according to the associated converted metadata values. The 3D anatomical image may be reconstructed by 3D reconstruction code executed by processor(s).

As discussed herein, Inventors discovered that the accuracy of the 3D anatomical image reconstructed from the formatted extracted 2D images slices and optionally according to the associated converted metadata values, is sufficiently accurate with respect to the original 3D anatomical mage (e.g., DICOM® image).

At 324, the reconstructed 3D image may be further processed and/or analyzed, for example, using computer aided diagnosis (CAD) code, and/or surgical simulation code. The reconstructed 3D image may be pre-processed prior to the analysis by the other application, for example, undergoing a sharpening process, and/or histogram stretch process.

Referring now back to FIG. 4, at 402, a current frame(s) of a video stream of a certain medical UI presented on a certain display of a certain client terminal is captured by a certain computing device. The computing device is connected for capturing frames of the video stream as described herein, for example, with reference to FIG. 2 and/or act 304 of FIG. 3. Capturing of frames from the video stream is performed, for example, as describe herein with reference to act 306 of FIG. 3.

At 404, the captured certain frame is analyzed to identify one or more data elements. The data element(s) may be extracted, for example, stored as sub-imagers of the frame. Each data element is indicative of a respective medical parameter of the patient. Exemplary parameters include, for example, ECG plot, SpO2, respiration rate, and heart rate.

Optionally, the data element(s) is non-text data. Exemplary non-text data includes: plot (e.g., graph) of a medical parameter as a function of time over a time interval, and/or region of an image representation of the respective frame, tables, and images.

Optionally, the data element(s) are target data elements, selected and/or predefined from multiple data elements appearing in the frame.

The part of the 2D frame that includes the target data elements may be identified, for example, based on a set of rules that define the data element(s) (e.g., according to location on the display, according to pixel values), based on manual settings defined by a user (e.g., application engineer installing the computing device and/or based on manufacturer settings), and/or based on trained classifier and/or segmentation code that segments the data element(s) from the captured frame.

At 406, the data element(s) are converted into converted value(s), optionally metadata value(s). Optionally, the converted metadata value(s) are represented as text data, where the text data is a representation of the non-text data. For example, the text data may represent one or more parameters of a plot of medical parameters over time, for example, maximum value of the medical parameter (e.g., currently appearing in the graph and/or over a historical time interval), minimum value of the medical parameter, standard deviation of the medical parameter, frequency of the medical parameter, text base meaning (i.e., interpretation) of the of the medical parameter. An example of the text based meaning of the medical parameter, for the case of an ECG plot, includes: normal sinus rhythm, tachycardia, atrial flutter, arrhythmia, ST depression detected, and ST elevation detected.

Optionally, the conversion from non-text data to text data is computed by a classifier (e.g., trained on a training dataset of non-text data labeled with text data), and/or optical character recognition code that detects image representation of characters in the respective frame and converts the detected image representation to a text representation of the characters. Exemplary classifiers include: one or more neural networks of various architectures (e.g., artificial, deep, convolutional, fully connected), support vector machine (SVM), logistic regression, k-nearest neighbor, and decision trees.

At 408, acts 402-406 are performed for each of multiple medical UIs presented on respective displays of respective client terminals. The acts may be independent performed by respective computing devices installed for each corresponding display and/or client terminal. The acts may be performed in parallel, overlapping in time, independently, and/or substantially simultaneously. The acts are performed for each display and/or client terminal such that resulting converted metadata value(s) are available for comparison, as described herein.

In one implementation, a display of a client terminal presents a medical monitoring application monitoring multiple medical parameters of a patient (e.g., ECG, artificial ventilator, pulse oximeter), and another display of another client terminal presents a medical UI of a medical database storing medical records, for example, an electronic medical record (EMR) application storing an EMR of the patient, and a PACS viewer presenting a list of stored patient images.

At 410, the converted metadata values obtained from the multiple medical UIs (presented on the multiple displays of the multiple client terminals) are analyzed to identify one or more baseline parameters.

Optionally, the baseline parameter(s) may be identified by finding a match and/or correlation between converted metadata value(s) from one display and converted metadata value(s) of another display. For example, the baseline parameter(s) is identified according to a correlation (e.g., match, corresponding values) between a patient identification (e.g., name, patient ID, government issued ID number) presented within the medical UI of the medical monitor application and the patient identification presented within the medical UI of the EMR application. Such matching baseline may be used, for example, to match between the EMR record of the patient and the monitoring data obtained by the monitoring device.

Alternatively or additionally, the baseline parameter(s) may be identified as one or more medical parameters, optionally, obtained from a medical database and/or from medical monitoring device. For example, value(s) of medical parameters obtained from the EMR. For example, values of monitoring parameters obtained from the medical monitoring device and/or other obtained values obtained stored in the EMR, for example, a reading of a previously obtained ECG, and an abnormal oxygen level reading obtained by a pulse oximeter.

Alternatively or additionally, one or more baseline parameters are obtained by monitoring and analyzing multiple frames of a single display. The multiple frames may be historical frames presented within a certain medical UI presented on the single display over a historical time interval. The multiple frames are analyzed, for example, by analyzing changes in values of the converted metadata values. For example, when a text description of the ECG extracted from the frames indicates ST segment depression over the multiple frames over the historical time interval, the ST segment depression (e.g., indicating a previous heart attack) is set as baseline. In another example, when the pulse oximeter measured oxygen saturation over the multiple frames is found to be within the range 88-92% (e.g., for COPD patients), the range 88-92% is set as baseline.

The analysis of for identifying of the baseline based on converted metadata values obtained from the multiple medical UIs may be performed, for example, by a central server that receives data streamed from multiple computing devices (e.g., over a network), an ad-hoc network which may be negotiated between the computing devices associated with the medical UIs, and/or a master-slave relationship where one computing device is designated as master for performing the analysis to determine the baseline based on locally computed converted metadata values (i.e., computed by the master) and converted metadata values received from the slave computing device.

At 412, multiple frames captured from the video stream may be monitored. The frames of one or more displays may be monitored. For example, the frames of a single display may be monitored, with frames of the other display(s) being ignored, such as once the baseline has been set based on the other display(s). In another example, the frames of all displays are monitored.

Frames may be monitored by iterating acts 402-406, for iteratively computing the converted metadata value(s). The converted metadata value(s) may be monitored over time, according to the monitored frames.

Optionally, frames are monitored for detecting manual entry of data by a user using the respective medical UI. The manual entry may be monitored, for example, by comparing current frames to one or more historical frames to detect changes. The changes may denote user entries. In another example, fields designated for manual user entry are identified and monitored. Such fields may be designated, for example, based on manual settings of an operator (e.g., application engineer), and/or classifier designed to identify such fields automatically, for example, based on appearance of the field (e.g., box) and/or based on tags associated with the field that are previously known to be associated with data that is manually entered, for example: patient name, rate of delivery, home address, name of medication being delivered.

At 414, a deviation from one or more of the baseline parameters is detected. The deviation may be detected according to a set of rules. The set of rules may be defined, for example, manually by an operator, according to set clinical guidelines, and/or automatically by code.

Optionally, the deviation of the monitored converted metadata value(s) from the baseline parameter(s) is detected.

Optionally, the deviation is of one or more medical parameters measured by the medical monitoring device (which are converted into the metadata value(s)).

For example, the set of rules defines a statistical distance threshold and/or time interval during which the distance is above the threshold, for the converted metadata value(s) to be defined as having deviated. For example, heart rate >100 for at least 30 seconds, or ST segment elevation for any period of time, or oxygenation percentage measured by pulse oximeter <92% for at least 10 seconds.

Alternatively or additionally, the detected deviation is of the monitored user entry, optionally according to a set of rules. For example, detecting incorrect data entered by the user (e.g., patient name does not match the EMR of the patient with same ID), erroneous data entered (e.g., illogical values), and/or no data entered (e.g., a defined time interval has passed without the user supplying input, for example, 30 seconds, or 1 minute, or other values).

The set of rules may define target desired behavior. A deviation from the set of rules may be indicative of lack of compliance by the user in performing according to the target desired behavior. Alternatively or additionally, the set of rules may define optimal desired target behavior. A deviation from the set of rules may be indicative of lack of optimal performance, or lack of knowledge of the user in performing the operation. In such cases, the generated instructions (i.e., generated in act 416) may direct the user to the target desired behavior and/or optimal behavior, for example, by injection of comments as an overlay of the medical UI.

The set of rules may define normally operating medical UIs. A deviation from the set of rules may be indicative of attempted malicious behavior, for example, a malware splash screen, unauthorized IT activity (e.g., command line window opening, failed logins), and/or attempt at harming the patient by entry of inappropriate data (e.g., dangerous levels of medication). The generated instructions (i.e., generated in act 416) may include, for example, an alert to the IT administrator, an alert to the cybersecurity professional, and/or triggering of an automated malware detection process.

The set of rules may define allowable entry of data. A deviation from the set of rules may be indicative of improper data entry. For example, a misspelled medication, and/or unreasonable amount of medication. The generated instructions (i.e., generated in act 416) may include, for example, an injection of a graphical overlay indicating the detected error, and/or a comment balloon suggesting how to fix the error. For example, a list of possible medications, to aid the user in choose which medication was actually meant.

In an example, the baseline parameter(s) are values for previously measured medical parameters obtained from the EMR of the patient, optionally found by correlating the patient ID and medical parameters being measured by a medical monitoring UI of one display with the EMR of the same patient ID on another display. The converted metadata values of the medical parameters measured by the monitoring device are obtained from the captured frames and a deviation from the baseline parameter(s) is detected.

At 416, instructions are generated based on the detected deviation.

Exemplary instructions include: storing an indication of the deviation in the EMR of the patient, an alert message for presentation on a screen of another computing device, and injecting a graphical overlay alert for presentation over the certain medical UI presented on the certain display.

The overlay may be injected into the video stream, and provided to the display for presentation. The overlay injection is performed without requiring installation of additional code at the client terminal and/or at a server hosting the medical UI application. The injection does not affect performance of the client terminal. The injection does not utilize processing and/or memory and/or data storage resources of the client terminal.

The graphical overlay may be injected for presentation over the certain medical UI associated with a location of the manual entry of data, indicative of, for example, an error in the manual entry of data, and a recommendation for correction of the error. The injected overlay may be an indication of the detected deviation, for alerting a healthcare provider. The graphical overlay may include, for example, a distinct color, an inverted color, a highlighting, an icon (e.g., arrow, star), and/or a comment balloon.

Alternatively or additionally, instructions are generated independently of the detected deviation. For example, instructions for storing an indication of the collected metadata values (e.g., summary thereof) in the EMR of the patient, for example, storing a text summary of the ECG monitoring graph of the patient over the last 2 hours. In another example, instructions are generated for extracting converted metadata from one medical UI (e.g., radiology information system) for entry into another medical UI (e.g., of a monitoring device). In yet another example, instructions are generated for collecting relevant converted metadata vales from multiple medical UIs, and storing the collected converted metadata values in a single data storage location (e.g., patient EMR), optionally in an aggregated form. In yet another example, instructions are generated for automatically generating a report based on the collected converted metadata values, for example, text summary of the ECG monitoring over the last 30 minute.

The generated instructions may include sending an alert indicative of the detected deviation, for example, to a mobile device of the supervising healthcare professional, to a display of another server (e.g., nurse monitoring station), and sending an email.

At 418, instructions are generated, emulating manual user entry using a user interface.

Optionally, the instructions for emulating manual user entry are generated based on the detected deviation from baseline. The instructions for emulating manual user entry may be for adjustment of the medical UI based on the detected deviation, for example, when a deviation is detected in one medical UI, a dose of medication may be changed by the emulated manual entry using another UI with the goal of eliminating the deviation. In another example, when no deviation is detected from baseline, optionally over a defined time interval, the instructions for emulation of manual entry are generated accordingly. For example, when the blood pressure of the patient has been within normal range for the last 2 hours, the frequency of measurement of the blood pressure may be lowered by the emulated manual entry using the UI.

Alternatively or additionally, the instructions for emulating manual user entry are generated independently of the detected deviation from baseline. For example, instructions may be automatically generated filling in patient information on one UI based on patient information extracted from another UI. For example, filling in patient data on a medical monitoring device based on the patient EMR.

At 420, one or more acts 402-418 are iterated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant displays and client terminals will be developed and the scope of the terms display and client terminals are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A medical imaging processing device for reconstruction of a 3D anatomical image from captured 2D frames presented on a display of a client terminal, the medical imaging processing device being external to the display and the client terminal, comprising:

at least one hardware processor executing a code for:
iteratively generating instructions for iterative adjustment of at least one presentation parameter of a 2D frame of the 3D anatomical image presented on the display, for creating a sequence of adapted 2D frames of the 3D anatomical image, the instructions transmitted from the medical imaging processing device to a physical input interface of at least one of the client terminal and display, wherein the instructions are for iteratively scrolling through parallel 2D frames of the 3D anatomical image for capturing the sequence of adapted 2D frames of the 3D anatomical image; for each respective 2D frame:
capturing the respective 2D frame from video signals transmitted from the client terminal to the display;
analyzing the respective captured 2D frame for extraction of a 2D anatomical image;
analyzing the respective captured 2D frame to identify at least one metadata element;
converting the at least one metadata element into at least one converted metadata value; and
formatting a plurality of the extracted 2D anatomical images and associated plurality of converted metadata values for reconstruction of the 3D anatomical image.

2. The medical imaging processing device of claim 1, wherein the medical data processing device is connected at least one of: (i) in-line between the client terminal and the display for capturing the video signals transmitted from the client terminal to the display, and (ii) to an outlet splitter port that outputs the video signals indicative of data presented on the display, and further comprising a component emulating a physical user interface for connecting to the physical input interface, for transmitting instructions emulating manual actions performed by a user manually reviewing the 3D anatomical image.

3. The medical imaging processing device of claim 1, wherein the 3D anatomical image is stored according to a format based on the DICOM® protocol, and wherein the display presents the 3D anatomical image within a PACS image viewer interface.

4. The medical imaging processing device of claim 1, further comprising code for:

reconstructing the 3D anatomical image according to the formatted plurality of extracted 2D images slices and associated plurality of converted metadata values; and analyzing the reconstructed 3D image using computer aided diagnosis (CAD) code.

5. The medical imaging processing device of claim 1, wherein the plurality of converted metadata values includes metadata used for the 3D reconstruction, including at least one member selected from the group consisting of: 2D slice thickness, accumulated number of 2D slices, spacing between 2D slices, histogram window, imaging modality mode, serial number of anatomical imaging device that captured the imaging data presented as the plurality of 2D slices, version of software, study instance UID, series instance UID.

6. The medical imaging processing device of claim 1, wherein the 3D anatomical image is stored with a bit depth that is greater than a bit depth of the presented 2D frames of the 3D anatomical images, wherein the instructions are for adapting each respective 2D frame for capturing a plurality of variations of each respective 2D frame, and wherein the plurality of variations of each respective frame are processed into a single 2D image having bit depth equal to the bit depth of the stored 3D anatomical image.

7. The medical imaging processing device of claim 1, wherein the instructions are for adapting at least one of: contrast settings, range settings, and window settings, of each respective 2D frame for capturing the plurality of variations of each respective 2D frame.

8. The medical imaging processing device of claim 1, further comprising a network interface for transmitting the formatted plurality of images and associated plurality of converted metadata values over a network to a server computing the reconstruction of the 3D anatomical image.

9. The medical imaging processing device of claim 1, wherein the at least one metadata element is a sub-portion of the 2D frame denoting text, and the at least one converted metadata value comprises a text representation of the sub-portion of the 2D frame converted by an optical character recognition process.

10. A medical data processing device for generation of instructions based on data presented within a plurality of medical UIs presented on a plurality of display of a plurality of client terminal, comprising:
at least one hardware processor executing a code for:
capturing a certain frame of a video stream of a certain medical UI presented on a certain display of a certain client terminal;
analyzing the certain frame to identify at least one data element, each data element is indicative of a respective medical parameter of a plurality of medical parameters;
converting the at least one data element into at least one converted metadata value;
analyzing the at least one converted metadata value with respect to another set of at least one converted metadata value obtained from at least one other medical UI presented on at least one other display of at least one other client terminal, to identify at least one baseline parameter;
monitoring a plurality of frames captured from the video stream for detecting, according to a set of rules, a deviation from the at one baseline parameter; and
generating instructions according to the deviation, wherein the instructions comprise at least one of: storing an indication of the deviation in an EMR of the patient, transmitting an alert message for presentation on a screen of another computing device, and injecting an overlay alert for presentation over the certain medical UI presented on the certain display.

11. The medical data processing device of claim 10, wherein the certain client terminal comprises a medical monitoring application monitoring a plurality of medical parameters of a patient, and the at least one other medical UI comprises an electronic medical record (EMR) application storing an EMR of the patient, wherein the at least one baseline parameter is identified according to a correlation between a patient identification presented within the medical UI of the medical monitor application and the patient identification presented within the medical UI of the EMR application.

12. The medical data processing device of claim 10, wherein the certain client terminal comprises a medical monitoring application monitoring a plurality of medical parameters of a patient, and the at least one other medical UI comprises an electronic medical record (EMR) application storing an EMR of the patient, wherein the at least one baseline parameter comprises a plurality of values for the plurality of medical parameters obtained from the EMR, wherein the plurality of frames are monitored to detect a deviation relative to the at least one baseline parameter of the plurality of medical parameters being monitored by the medical monitoring application.

13. The medical data processing device of claim 10, wherein the certain client terminal comprises a medical monitoring application monitoring a plurality of medical parameters of a patient, and the at least one other medical UI comprises an electronic medical record (EMR) application storing an EMR of the patient, wherein the at least one baseline parameter comprises a plurality of values for the plurality of medical parameters obtained from the EMR, wherein the plurality of frames are monitored to detect a deviation relative to the at least one baseline parameter of the plurality of medical parameters being monitored by the medical monitoring application.

14. The medical data processing device of claim 10, further comprising code for:
capturing a plurality of historical frames presented within the certain medical GUI presented on the certain display;
analyzing the plurality of frames to compute the at least one baseline parameter;
monitoring a plurality of future frames presented on the certain display of the certain client terminal for detecting, according to the set of rules, the deviation from the at one baseline parameter.

15. The medical data processing device of claim 10, wherein the at least one data element comprises non-text data, and wherein the at least one converted value comprises text data representing the non-text data.

16. The medical data processing device of claim 15, wherein the non-text data is selected from the group consisting of: plot of a medical parameter as a function of time over a time interval, and region of an image representation of the respective frame.

17. The medical data processing device of claim 15, wherein the conversion from non-text data to text data is computed by at least one of: classifier trained on a training dataset of non-text data labeled with text data, and optical character recognition code that detects image representation of characters in the respective frame and converts the detected image representation to a text representation of the characters.

18. The medical data processing device of claim 10, further comprising:
- monitoring at least the certain frame to identify manual entry of data by a user using the certain medical UI;
- analyzing the manual entry of data for detecting a deviation according to a set of rules; and
- generating instructions for presentation of an overlay over the certain medical UI associated with a location of the manual entry of data, indicative of at least one of: an error in the manual entry of data, and a recommendation for correction of the error.

* * * * *